(12) United States Patent
Metzler et al.

(10) Patent No.: US 12,343,493 B2
(45) Date of Patent: Jul. 1, 2025

(54) SYSTEMS AND METHODS FOR ACCESSING A SITE WITHIN THE BODY

(71) Applicant: The Regents of the University of California, Oakland, CA (US)

(72) Inventors: Ian Metzler, San Francisco, CA (US); Thomas Chi, San Francisco, CA (US); Pierre Nedelec, Oakland, CA (US); Woojoo Kim, Oakland, CA (US); Anshal Gupta, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 794 days.

(21) Appl. No.: 17/413,318

(22) PCT Filed: Dec. 11, 2019

(86) PCT No.: PCT/US2019/065775
§ 371 (c)(1),
(2) Date: Jun. 11, 2021

(87) PCT Pub. No.: WO2020/123690
PCT Pub. Date: Jun. 18, 2020

(65) Prior Publication Data
US 2022/0008707 A1    Jan. 13, 2022

Related U.S. Application Data

(60) Provisional application No. 62/777,885, filed on Dec. 11, 2018.

(51) Int. Cl.
*A61M 25/10* (2013.01)
*A61M 29/02* (2006.01)
*A61M 39/02* (2006.01)

(52) U.S. Cl.
CPC ........ *A61M 39/0247* (2013.01); *A61M 29/02* (2013.01); *A61M 2029/025* (2013.01);
(Continued)

(58) Field of Classification Search
CPC ....... A61B 17/3439; A61B 2017/3486; A61M 2025/0004; A61M 29/02; A61M 2025/1081; A61M 25/0032
See application file for complete search history.

(56) References Cited

U.S. PATENT DOCUMENTS 4,601,713 A    7/1986    Fuqua
5,395,349 A    3/1995    Quiachon et al.
(Continued)

OTHER PUBLICATIONS

International Search Report dated Mar. 2, 2020 in co-pending PCT Application No. PCT/US2019/065775 filed Dec. 11, 2019.

*Primary Examiner* — Deanna K Hall
(74) *Attorney, Agent, or Firm* — Risley IP; David R. Risley (57) ABSTRACT

In one embodiment, an expandable access sheath including a planar sheet of material that is configured to be rolled up around an inflatable balloon, the sheet comprising an inner surface, an outer surface, a leading edge, a trailing edge, a proximal edge, and a distal edge, the sheet further including at least one locking tab that extends from either the inner surface or the outer surface of the sheet, wherein the leading edge of the sheet is configured to interface with the locking tab to lock the access sheath in a predetermined configuration in which the access sheath forms an inner working channel having a predetermined cross-sectional dimension after the access sheath has been expanded by the inflatable balloon.

18 Claims, 11 Drawing Sheets

(52) U.S. Cl.
CPC .............. *A61M 2039/0291* (2013.01); *A61M 2039/0297* (2013.01)

(56) References Cited

U.S. PATENT DOCUMENTS

| | | |
|---|---|---|
| 5,997,508 A | 12/1999 | Lunn et al. |
| 6,090,072 A | 7/2000 | Kratoska et al. |
| 7,481,803 B2 | 1/2009 | Kesten et al. |
| 2001/0012950 A1* | 8/2001 | Nishtala ............ A61M 25/0662 606/198 |
| 2005/0222576 A1* | 10/2005 | Kick .................. A61B 17/3439 606/104 |
| 2006/0052750 A1* | 3/2006 | Lenker ............... A61B 17/3439 604/164.01 |

* cited by examiner

SYSTEMS AND METHODS FOR ACCESSING A SITE WITHIN THE BODY

CROSS-REFERENCE TO RELATED APPLICATION

This application is the 35 U.S.C. § 371 national stage application of PCT Application No. PCT/US2019/065775, filed Dec. 11, 2019, where the PCT claims the benefit of and priority to U.S. Provisional Application Ser. No. 62/777,885, filed Dec. 11, 2018, both of which are herein incorporated by reference in their entireties.

BACKGROUND

Kidney stone disease, also known as urolithiasis, is a condition in which one or more solid pieces of material, referred to as kidney stones, develop within the urinary tract. Kidney stones typically form in the kidney and often leave the body naturally in the urine stream. If a kidney stone grows large in size, however, it can cause blockage of the ureter and severe pain in the lower back or abdomen.

There are various procedures available for removing kidney stones that cannot be naturally passed by the body. One such procedure is percutaneous nephrolithotomy in which the kidney is accessed through a percutaneous incision. In this procedure, a narrow passage is formed through the soft tissues (skin, fascia, and muscle) of the back to access the collecting system of the kidney in which the kidney stone or stones reside. Once such access is achieved, the stone(s) can be broken up into smaller fragments and removed through the passage.

In the typical percutaneous nephrolithotomy procedure, a hollow needle is inserted through the back into the collecting system of the kidney and a guidewire is then passed through the needle. Once the guidewire is in place, the needle is removed and the passage can then be dilated to provide enough space to pass instruments through the passage and remove the kidney stone fragments. In some cases, the passage is initially dilated by sequentially passing multiple rigid dilators of increasing size over the guidewire to gradually expand the passage. Once this "pre-dilation" has been performed, an inflatable dilator that has an initial small diameter can be passed over the guidewire and expanded by filling it with a fluid, such as saline, to complete the dilation of the passage. At this point in the procedure, the pressure within the inflatable dilator can be reduced to enable an access sheath to be passed over the dilator. Once in place, the access sheath maintains the passage in the dilated state and creates a working channel that facilitates removal of the kidney stone fragments.

While the above method is viable, it has several disadvantages. First, having to pass multiple rigid dilators through the soft tissues can cause unnecessary trauma to the soft tissues of the patient and, therefore, unnecessary damage to the tissues. In addition, it can be difficult to pass the access sheath between the soft tissues and the inflatable dilator, which can result in further tissue damage. Furthermore, having to use multiple dilators, including both rigid and inflatable dilators, greatly increases the number of steps of the procedure and, therefore, increases the time and complexity of the procedure. The multitude of steps also increases the likelihood of the guidewire falling out, patient bleeding, or worsening the quality of the imaging used for guiding the procedure. Moreover, with such a procedure, the surgeon must select the size of the access sheath that will be used before the procedure is performed and cannot later change (e.g., expand) the sheath after it is in place.

In view of the above discussion, it can be appreciated that it would be desirable to have a system and method for accessing a site within the body, such as the collecting system of the kidney, which does not suffer from the disadvantages of conventional procedures.

SUMMARY OF THE DISCLOSURE

In one embodiment, an access assembly comprises an inflatable balloon having a first internal passage configured to receive a guidewire; a dilation tip mounted to the inflatable balloon, the dilation tip having a second internal passage aligned with the first passage that is also configured to receive a guidewire; and an expandable access sheath wrapped around the inflatable balloon; wherein the access sheath is configured to expand when the balloon is inflated so as to form an inner working channel through which a surgical procedure can be performed.

In some embodiments, the expandable access sheath comprises a flexible planar sheet of material that is rolled up to form a cylindrical tube, the sheet comprising an inner surface and an outer surface.

In some embodiments, the sheet further comprises at least one locking tab that extends from the inner side or the outer side of the sheet that is configured to interface with a leading edge of the sheet to lock the access sheath in a predetermined configuration in which the working channel has a predetermined cross-sectional dimension.

In some embodiments, the locking tab extends from the inner side of the sheet.

In some embodiments, the locking tab extends from the outer side of the sheet.

In some embodiments, the leading edge comprises a beveled portion that is configured to mate with the locking tab.

In some embodiments, the leading edge further comprises a bulbous portion inward of the beveled portion, the bulbous portion being configured to form a smooth transition between the locking tab and the surface of the sheet.

In some embodiments, the sheet comprises multiple locking tabs positioned at discrete positions along the inner or outer surface of the sheet so as to be configured to lock the access sheath in multiple predetermined configurations, each forming an inner working channel having a predetermined cross-sectional dimension.

In some embodiments, the locking tab comprises multiple spaced locking tab segments that are linearly aligned with each other so as to form the locking tab.

In some embodiments, the assembly further comprises an elastic outer casing wrapped around the expandable access sheath.

In one embodiment, an expandable access sheath comprises a flexible planar sheet of material that is configured to be rolled up around an inflatable balloon, the sheet comprising an inner surface, an outer surface, a leading edge, a trailing edge, a proximal edge, and a distal edge, the sheet further comprising at least one locking tab that extends from either the inner surface or the outer surface of the sheet, wherein the leading edge of the sheet is configured to interface with the locking tab to lock the access sheath in a predetermined configuration in which the access sheath forms an inner working channel having a predetermined cross-sectional dimension after the access sheath has been expanded by the inflatable balloon.

In some embodiments, the locking tab extends from the inner side of the sheet.

In some embodiments, the locking tab extends from the outer side of the sheet.

In some embodiments, the leading edge comprises a beveled portion that is configured to mate with the locking tab.

In some embodiments, the leading edge further comprises a bulbous portion inward of the beveled portion, the bulbous portion being configured to form a smooth transition between the locking tab and the surface of the sheet.

In some embodiments, the sheet comprises multiple locking tabs positioned at discrete positions along the inner or outer surface of the sheet so as to be configured to lock the access sheath in multiple predetermined configurations, each forming an inner working channel having a predetermined cross-sectional dimension.

In some embodiments, the locking tab comprises multiple spaced locking tab segments that are linearly aligned with each other so as to form the locking tab.

In some embodiments, the leading edge is parallel with the trailing edge but the distal edge is angled relative to the proximal edge such that the access sheath forms a conical distal end when the access sheet is rolled up.

In one embodiment, a method for performing a surgical procedure comprises forming a passage through soft tissues of a subject to a site of interest at which the surgical procedure is to be performed; passing a guidewire through the passage; passing an access assembly over the guidewire and into the passage; inflating an inner inflatable balloon of the access assembly to cause an expandable access sheath surrounding the balloon to expand; locking the access sheath with locking elements of the access sheath in a predetermined configuration such that the access sheath forms an inner working channel having a predetermined cross-sectional dimension; deflating and removing the balloon from the working channel; and performing the surgical procedure at the site of interest with surgical instruments that are passed through the working channel.

In some embodiments, the access sheath comprises a flexible sheet of material that is rolled up around the inflatable balloon and the sheet unrolls as the balloon is inflated to form the working channel and the locking elements comprise at least one locking tab that extends from a side of the sheet and a leading edge of the sheet that is configured to mate with the locking tab.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have a system and method for accessing a site within the body that does not suffer from the disadvantages of existing procedures. Disclosed herein are examples of such systems and methods. In one embodiment, a system for accessing a site of interest (e.g., a surgery site) within the body comprises an access assembly that includes a dilation tip, an inflatable balloon upon which the tip can be mounted, and an expandable access sheath that surrounds the balloon. Such an assembly can be used both to dilate a passage that leads to the surgery site and establish a working channel through which a surgical procedure can be performed at that site. In some embodiments, the access assembly can be passed over a guidewire that leads to the surgery site. As the assembly is passed over the guidewire, the dilation tip dilates the soft tissue. Once the tip reaches the site of interest, the inflatable balloon can be inflated to further dilate the tissue. As the balloon inflates, it expands the access sheath, which is configured to lock at predetermined sizes (e.g., diameters). Once the access sheath has been expanded to the desired size, the balloon and the tip can be removed through the sheath, which is left in place to define and maintain a working channel. By using the access assembly in such a procedure, trauma to the surrounding tissues is greatly reduced. In addition, the size of the working channel formed by the access sheath can be adjusted (e.g., enlarged) in situ without the need to remove it and replace it with a larger access sheath.

In the following disclosure, various specific embodiments are described. It is to be understood that those embodiments are example implementations of the disclosed inventions and that alternative embodiments are possible. Such alternative embodiments can include "hybrid" embodiments that includes aspects of different embodiments. All such embodiments are intended to fall within the scope of this disclosure.

Figure 1A:
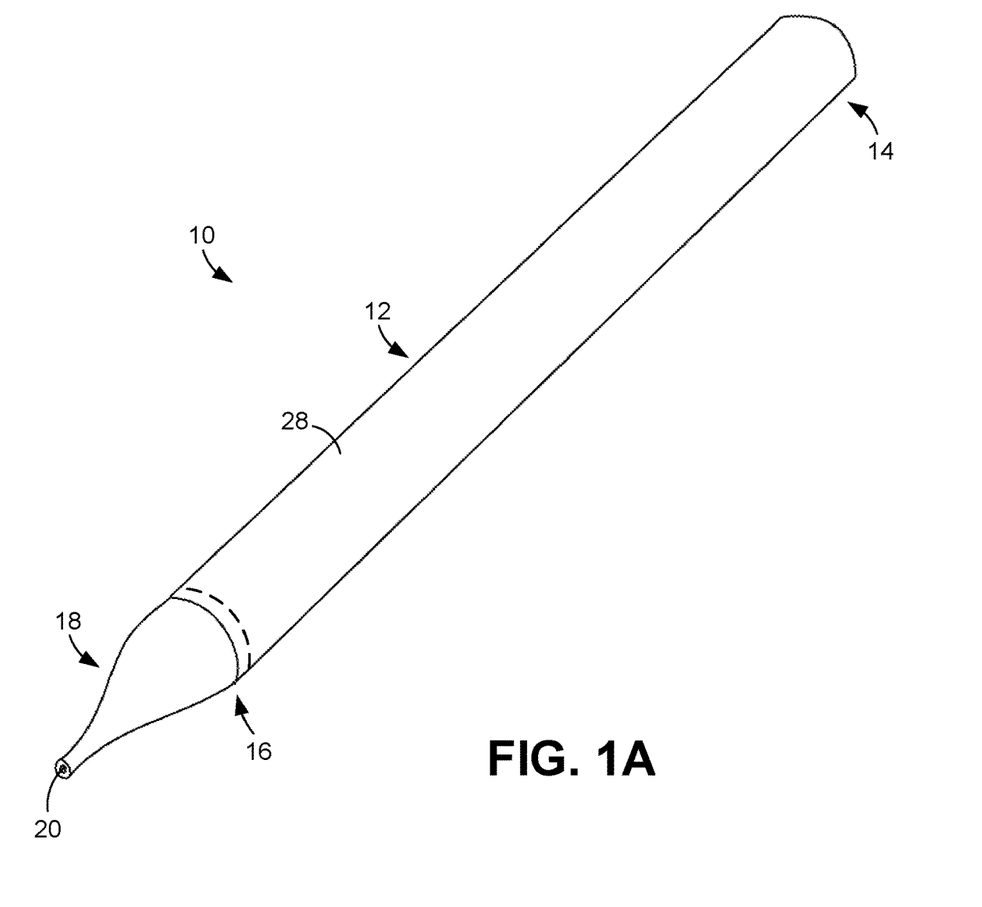
FIG. 1A is a perspective side view of an embodiment of an access assembly.

FIG. 1A illustrates an embodiment of a system for accessing a site of interest within the body. More particularly, illustrated is an embodiment of an access assembly 10 that can be used both to dilate a passage that leads to a surgery site and establish a working channel through which a surgical procedure can be performed at the site. Visible in FIG. 1A are an elongated body 12 of the assembly 10, which has a proximal end 14 and a distal end 16.

Figure 1B:
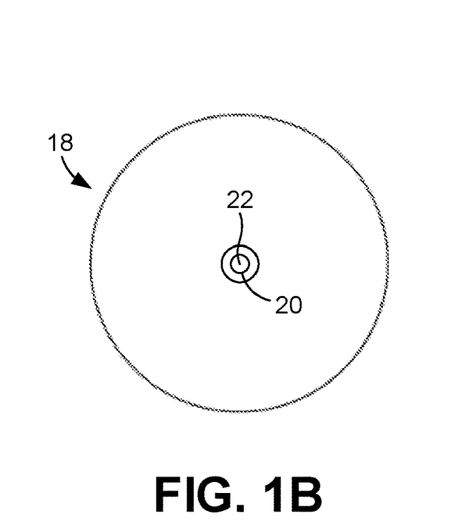
FIG. 1B is a distal end view of the access assembly of FIG. 1A.
Figure 1C:
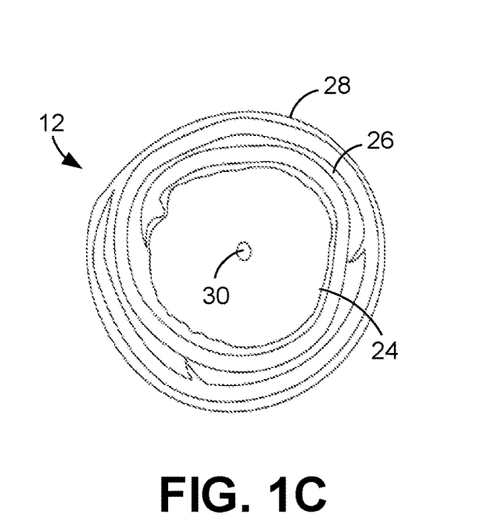
FIG. 1C is a proximal end view of the access assembly of FIG. 1A.
Figure 1D:
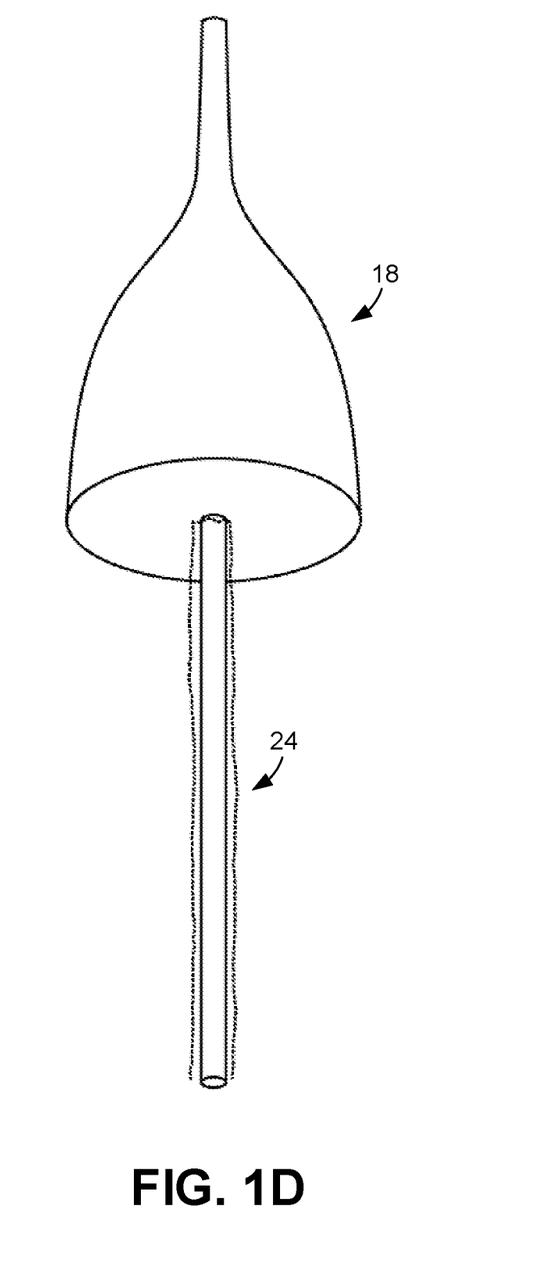
FIG. 1D is perspective side view of the access assembly of FIG. 1A with an access sheath of the assembly removed to reveal an inflatable balloon of the assembly.

With reference to FIGS. 1C and 1D, the body 12 includes an inner inflatable balloon 24 that is surrounded by an expandable access sheath 26, which is, in turn, surrounded by an elastic outer casing 28. Referring again to FIG. 1A, mounted to the distal end 16 of the body 12 is a dilation tip 18 that is configured to dilate tissue as the assembly 10 is passed over a guidewire that extends through a passage in the body that has, for example, been formed by a needle or other piercing instrument. As shown in FIG. 1A, the tip 18 is mounted to the distal end of the body 12 and the distal end of the outer casing 28 is attached (e.g., adhered) to the proximal end of the tip. In some embodiments, the tip 18 can be directly mounted to the distal end of the inflatable balloon 24, as shown in FIG. 1D. By way of example, the distal end of the balloon 24 can be inserted into an internal passage of the tip 18 (discussed below) with a friction fit. Alternatively or in addition, the tip 18 can be affixed to the distal end of the balloon 24 using suitable affixation means, such as adhesive or adhesive tape.

As shown in both FIGS. 1A and 1D, the dilation tip 18 is tapered so as to have a relatively small outer dimension (e.g., outer diameter) at its distal end and a relatively large outer dimension (e.g., outer diameter) at its proximal end. In some embodiments, the body 12 and the proximal end of the tip 18 are each approximately 3 to 7 mm in diameter (or equivalent dimension if they are not circular in cross-section). As shown in FIGS. 1A and 1B, the tip 18 has an opening 20 that leads to an internal passage 22 that extends along the length of the tip to an internal passage 30 of the balloon 24, shown in FIG. 1C. These passages 22, 30 together form a continuous passage that extends along the entire length of the assembly 10 and that is configured to receive a guidewire.

Figure 2:
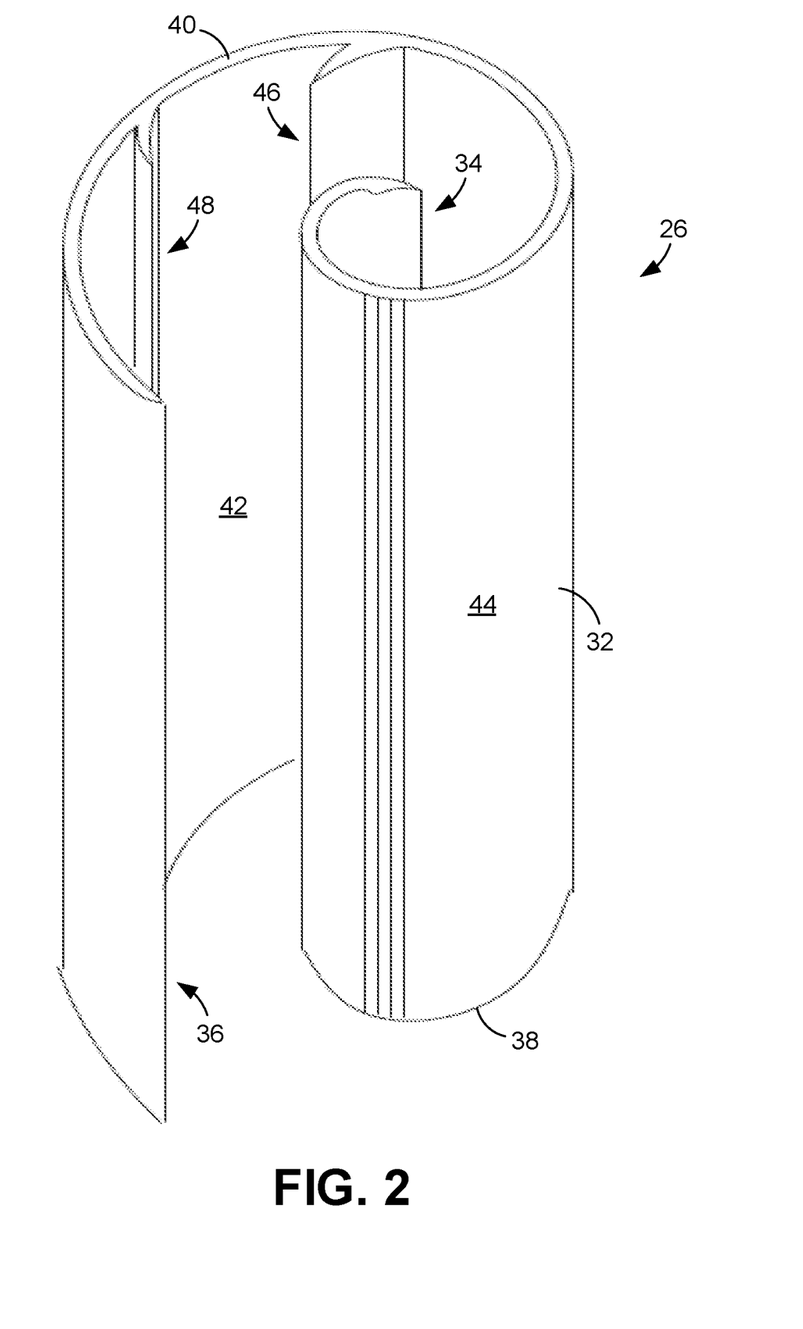
FIG. 2 is a perspective side view of an embodiment of an expandable access sheath of the access assembly of FIG. 1.

FIG. 2 shows the expandable access sheath 26 separate from the remainder of the access assembly 10. As can be appreciated from this figure, the access sheath 26 comprises a generally flexible and planar sheet 32 of material that can be rolled up to form an elongated cylindrical tube. The sheet 32 can be unitarily formed from a single piece of flexible material, such as a polymer or metal material. In some embodiments, the sheet 32 is made of nylon, polyamide, or polytetrafluoroethylene (PTFE). Notably, irrespective of what material is used, the access sheath 26, as well as the remainder of the components of the access assembly 10, is made of a biocompatible material that is appropriate for use within the body of a subject (e.g., patient) upon whom the procedure is to be performed.

In some embodiments, the sheet 32 can have a length dimension (in the vertical direction in FIG. 2) of approximately 10 to 30 cm, a width dimension (in the horizontal direction in FIG. 2) of approximately 3 to 5 cm, and a thickness of approximately 0.2 to 1 mm. While the access sheath 26 is described herein as comprising a "sheet" of material, it is noted that the sheath need not be fabricated as a sheet of material. For example, in some embodiments, the sheet 32 can be obtained by initially forming an elongated tube (e.g., using an extrusion process) and then slitting the tube on one side along its longitudinal direction. When the slit tube is flattened, it can be said to form a planar sheet of material. Accordingly, the term "sheet," as used herein, is not intended to identify the manner in which the access sheath 26 is made.

With further reference to FIG. 2, the sheet 32 includes leading edge 34, a trailing edge 36, a proximal edge 38, and a distal edge 40. When the sheet 32 is rolled up so as to form a cylindrical tube that can be used to create a working channel, the leading edge 34 may be described as the inner edge of the sheath, the trailing edge 36 may be described as the outer edge of the sheath, the proximal edge 38 forms the proximal end of the sheath, and the distal edge 40 forms the distal end of the sheath. In addition to its various edges, the sheet 32 also comprises an inner side 42 that forms an inner working channel, and an outer side 44 that forms an outer surface of the sheath.

Figure 3:
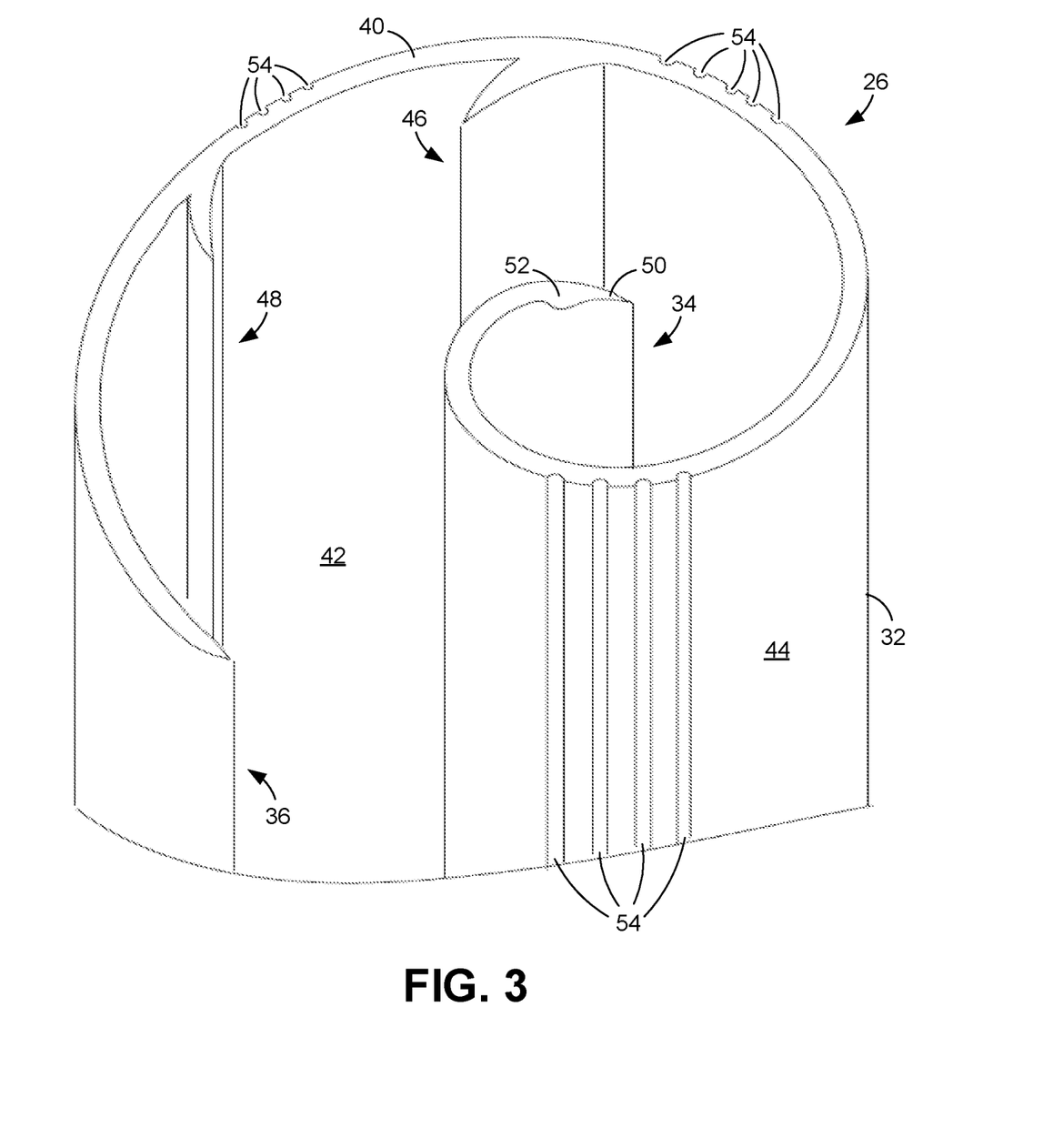
FIG. 3 is a detail perspective view of the access sheath of FIG. 2.

With reference next to the detail view of FIG. 3, provided on the inner side 42 of the sheet are first and second locking tabs 46 and 48 that, along with the leading edge 36 of the sheet, comprise locking elements of the access sheath. In the illustrated embodiment, the locking tabs 46, 48 extend along the length direction of the sheet 32 and, therefore, the length direction of the access sheath 26, from the proximal edge 38 to the distal edge 40 of the sheet. The locking tabs 46, 48 each have generally triangular cross-sections and are configured to interface with the leading edge 34 of the sheet 32 to lock the access sheath 26 in predetermined sizes (e.g., diameters). As is apparent in FIG. 3, each locking tab 46, 48 is angled relative to the inner surface 42 of the sheet 32 so as to form a shallow angle with that surface. In some embodiments, the locking tabs 46, 48 each form an angle of approximately 20° to 50° relative to the inner surface 42. Such an angle ensures that the locking tabs 46, 48 do not extend very far radially inward into the working channel formed by the access sheath 26 and, therefore, do not interfere with the surgical procedure.

The first locking tab 46 is positioned along the inner surface 42 of the sheet 32 nearer to the leading edge 34 so as to be configured to lock the access sheath 26 in an orientation in which the sheath forms an inner working channel having a relatively small inner dimension (e.g., inner diameter). The second locking tab 48 is positioned along the inner surface 42 of the sheet 32 farther from the leading edge 34 (and nearer the trailing edge 36) so as to be configured to lock the access sheath 26 in an orientation in which the sheath forms an inner working channel having a relatively large inner dimension (e.g., inner diameter). By way of example, the first locking tab 46 can be used to form an 18 Fr (6 mm) working channel and the second locking tab 48 can be used to form a 24 Fr (8 mm) working channel. While the access sheath 26 is illustrated as having two locking tabs 46, 48 and, therefore, as being configured to form inner working channels of two sizes, it is noted that the access sheath can comprise a fewer or a greater number of locking tabs. For instance, in other embodiments, the access sheath 26 can have three locking tabs configured so as to create 18, 24, and 30 Fr (10 mm) working channels, respectively.

As depicted in FIG. 3, the leading edge 34 of the sheet 32 has a shape that is specifically configured to mate with the locking tabs 46, 48. In particular, the leading edge 34 comprises an outermost sharp beveled portion 50 that is also generally triangular in cross-section and that includes a bulbous portion 52 that is positioned inward of the beveled portion. During expansion of the access sheath 25 as the balloon 24 is inflated, the bulbous portion 52 provides pressure on the leading edge 34 to ensure it successfully mates with a locking tab 46, 48. In addition, the bulbous portion 52 creates a smooth transition at the interface of the locking tab 46, 48 and the leading edge 34 so that the working channel formed by the sheath 26 is smooth and, therefore, less likely to interfere with the surgical procedure.

In addition to the above-described features, the access sheath 26 can comprise one or more echogenic features that can assist the surgeon in visualizing the sheath under fluoroscopic or ultrasonic imaging. In the illustrated embodiment, the echogenic features comprise multiple groups of parallel linear grooves 54 formed in the outer surface 44 of the sheet 32 that extend longitudinally from the proximal edge 38 to the distal edge 40 of the sheet. It is noted that, when such grooves 54 are present, they may also facilitate rolling up of the access sheath 26.

The structure of the access assembly 10 having been described above, use of the assembly in a surgical procedure will now be discussed. While the access assembly 10 can be used to form a working channel within the soft tissues of a patient in substantially any procedure in which a site surrounded by the soft tissues is to be accessed, use of the assembly will be discussed below in the context of a percutaneous nephrolithotomy procedure as an example.

If one or more kidney stones are to be removed via percutaneous nephrolithotomy, a hollow needle is inserted through the patient's back into the collecting system of the kidney and a guidewire is passed through the needle. Prior to use, the access assembly 10 is in a "collapsed" orientation in which the inner inflatable balloon 24 is deflated, the access sheath 26 is tightly wrapped around the balloon, and the outer casing 28 is tightly wrapped around the sheath, as shown in FIG. 1A. The outer casing 28 of the access assembly 10 ensures that the access sheath 26 does not unintentionally expand, which would interfere with its insertion into the body. In addition, the outer casing 28 smooths the trailing edge 36 of the sheet 32 so as to avoid inflicting trauma on the patient's tissues. The outer casing 28 may also help affix the access sheath 26 to the dilation tip 18. Furthermore, the outer casing 28 may also have features, such as microbubbles or small irregular grooves, to make it more hyperechoic under ultrasound visualization. Moreover, as described below, the outer casing 28 may squeeze the access sheath 26 to assist in the locking of the sheath at a predetermined size (e.g., diameter).

After the needle has been removed, the passage in which the guidewire lies can be dilated using the access assembly 10. In particular, the access assembly 10 can be passed over the guidewire by passing the guidewire through the opening 20 provided in the dilation tip 18 and through the inner passages 22 and 30 formed by the tip and the inflatable balloon 24, respectively. As the access assembly 10 enters the passage in which the guidewire lies, the dilation tip 18 gently dilates the soft tissues that define the passage so as to provide space for the elongated body 12 of the assembly. Notably, this step is similar to the "pre-dilation" step that is often performed using a series of rigid dilators of increasing size. Unlike that step, however, multiple dilators do not need to be passed through and withdrawn from the patient's tissues multiple times. As such, trauma to those tissues is greatly reduced.

Figure 4A:
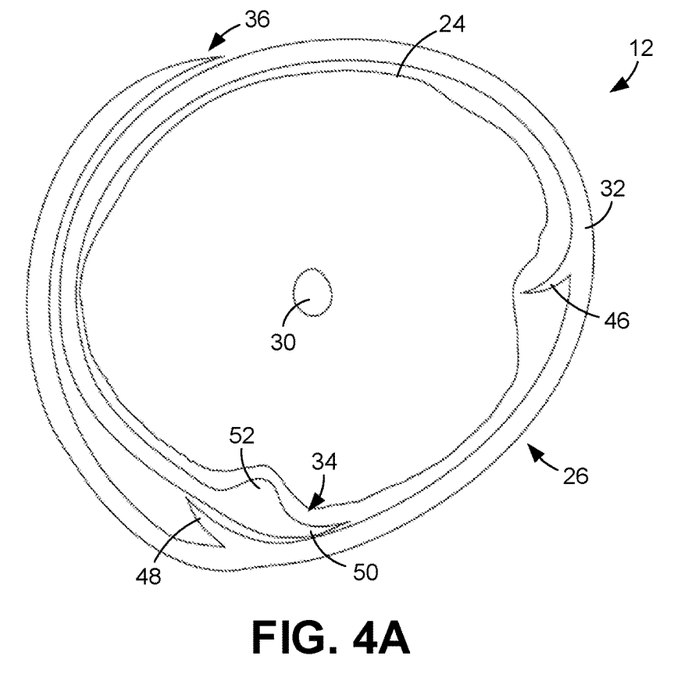
FIGS. 4A and 4B are sequential views that illustrate expansion and locking of the access sheath of FIG. 2 during use of the access assembly of FIG. 1.
Figure 4B:
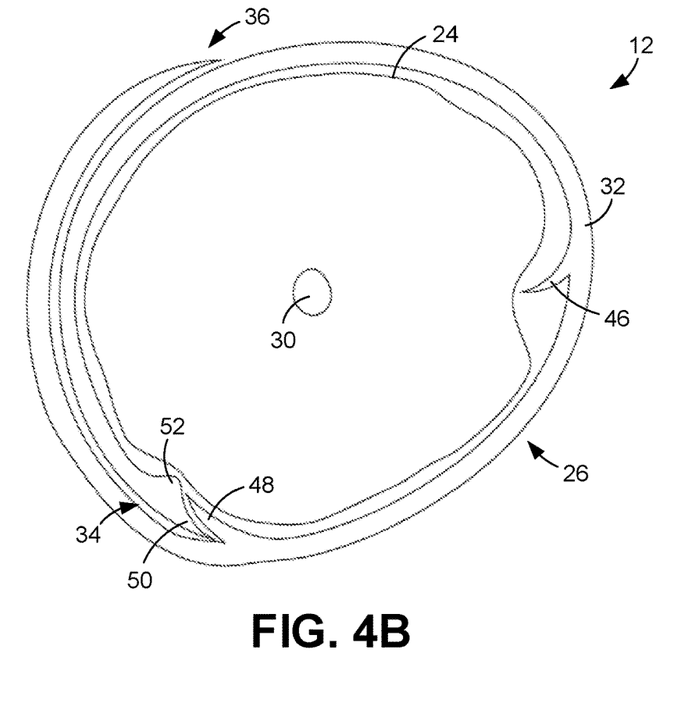

Once the dilation tip 18 has reached the collecting system of the kidney in which the kidney stone or stones reside, the inflatable balloon 24 can be expanded to simultaneously expand the access sheath 26 and dilate the soft tissues of the patient. As the outer casing 28 is elastic, it expands as the access sheath 26 expands. FIGS. 4A and 4B depict an example of expansion of the sheath 26 (the outer casing 28 is not shown in these figures). FIG. 4A shows the balloon 24 having been partially inflated to a point at which the access sheath 26 has expanded and, therefore, has unrolled, to a first degree. In the example of FIG. 4A, the leading edge 34 of the sheet 32 of the access sheath 26 has passed over the first locking tab 46 and is positioned in front of the second locking tab 48. As the balloon 24 is further inflated, the leading edge 34 will pass over the second locking tab 48. Assuming the user wishes to lock the sheath 26 with the second locking tab 48, the balloon 24 can then be partially deflated. Due to the presence of the elastic outer casing 28 and the surrounding soft tissues, the access sheath 26 is squeezed inward upon such deflation so as to cause the leading edge 34 to mate with (or lock to) the second locking tab 48, as shown in FIG. 4B. The result is an access sheath that is placed in a predetermined configuration and that forms a working channel having a predetermined cross-sectional dimension.

Figure 5:
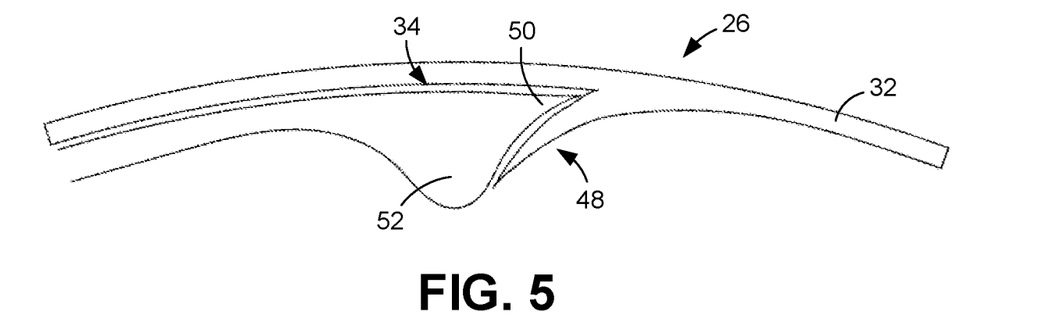
FIG. 5 is a detail side view illustrating a leading edge of the access sheath of FIG. 2 mating with a locking tab of the access sheath so as form an inner working channel having a predetermined size.

FIG. 5 is a detail view that illustrates such mating/locking. As indicated in that figure, the leading edge 34 occupies the space between the locking tab 48 and the inner surface 42 of the sheet 32 of the access sheath 26. In particular, the beveled portion 50 of the leading edge 34 occupies this space as it forms an angle that is similar to the angle formed between the locking tab 48 and the inner surface 42. In addition, the bulbous portion 52 interfaces with the balloon 24 as it is inflated to facilitate mating between the beveled portion 50 and the locking tab 48. In addition, the bulbous portion 52 forms a smooth transition between the outer edge of the locking tab 48 and the leading edge 34 so that the working channel formed by the access sheath 26 is smooth and, therefore, less likely to interfere with the surgical procedure.

Once the leading edge 34 has mated with one of the locking tabs 46, 48, no further dilation is needed. Notably, complete dilation will have been achieved without having to insert and withdraw multiple rigid dilators. As mentioned above, this reduces trauma to the patient, reduces the risk of losing access via the guidewire, and greatly reduces the number of steps that need to be performed. At this point, the inflatable balloon 24 can be fully deflated to facilitate its removal from the access sheath 26. In embodiments in which the dilation tip 18 is mounted to the distal end of the balloon 24, the tip 18, which is significantly smaller in outer dimension (e.g., diameter) than the working channel formed by the expanded sheath 26, is removed along with the balloon. Once the balloon 24 and the tip have been removed, a generally cylindrical access sheath 26 remains within the patient that defines a generally cylindrical working channel that provides access to the collecting system of the kidney. Significantly, the access sheath 26 will have been positioned within the body without having to pass it over an inflated balloon that is already resident within the body. This further reduces trauma to the patient's soft tissues.

Once a working channel that extends to the collecting system of the kidney has been established, the kidney stone(s) within the collecting system can be broken up into smaller fragments and those fragments can be removed via the working channel. If for any reason the surgeon decides that a larger working channel is needed during the procedure, and assuming there is a further locking tab available, the balloon 24 (or a new balloon or other dilating device) can be inserted into the working channel and expanded so as to further expand the access sheath 26 and enable its leading edge 34 to mate with the next locking tab. Accordingly, unlike conventional access sheaths, the access sheath 26 is adjustable and can be enlarged in situ without having to remove and replace the access sheath. Once again, this reduces trauma to the patient's tissues and blood loss during the transition.

After the one or more kidney stones have been removed, the access sheath 26 can be removed. This can be achieved in the same way as a standard sheath, in which the sheath is withdrawn from the passage and the patient's body, leaving a nephrostomy tube in place.

It is noted that various modifications can be made to the components of the access assembly to suit individual preferences or applications. Described below are alternative embodiments for the dilation tip and the expandable access sheath, as well as other components that can be used in conjunction with the access assembly.

Figure 6:
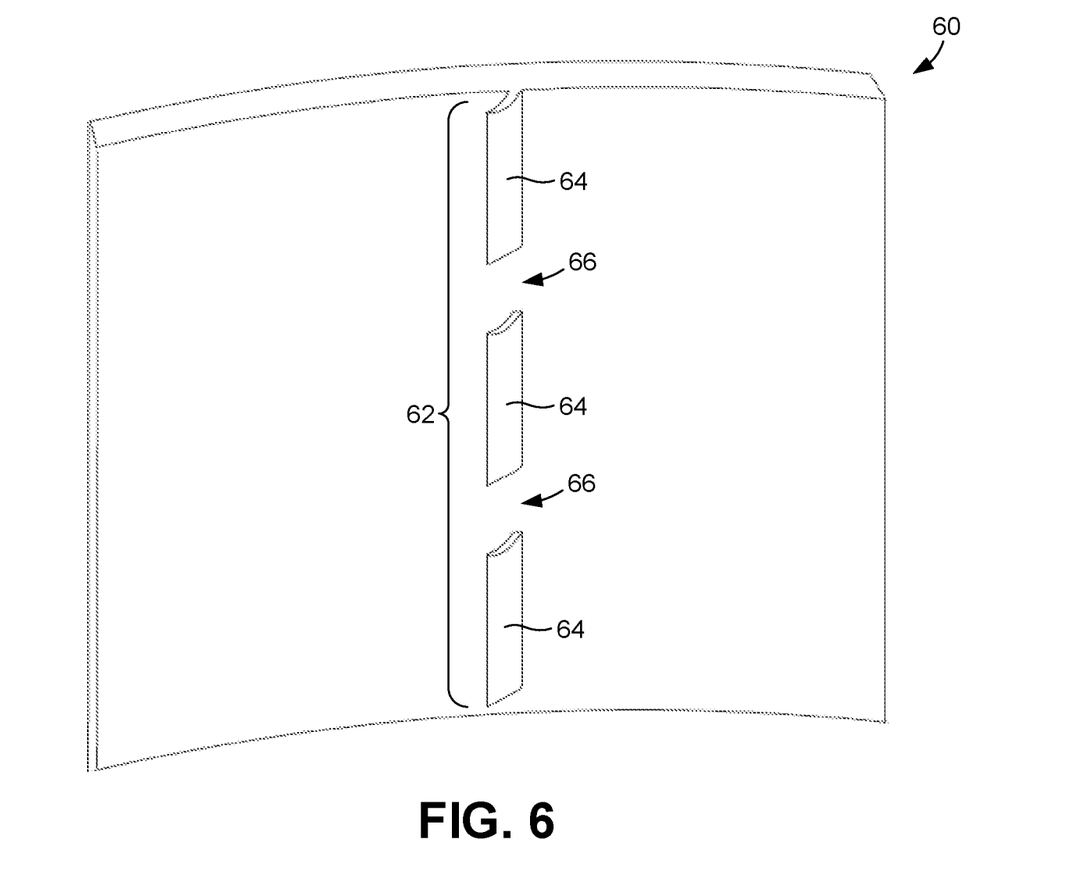
FIG. 6 is a partial perspective view of a first alternative expandable access sheath, the access sheath having a locking tab comprised of multiple tab segments.

FIG. 6 is a partial perspective view that illustrates a first alternative expandable access sheath 60. The access sheath 60 is similar to the access sheath 26 described above except that it implements an alternative configuration for the locking tabs. In this embodiment, multiple linearly aligned locking tab segments 64 separated by blank spaces 66 together form a locking tab 62. Such an embodiment may be useful in situations in which the leading edge (not shown) of the access sheath is not perfectly aligned with the locking tab 62. By providing multiple tab segments 64, the leading edge can initially mate with one or more of the tab segments 64 and later mate with the others so that mating with a continuous elongated locking tab is not required.

Figure 7A:
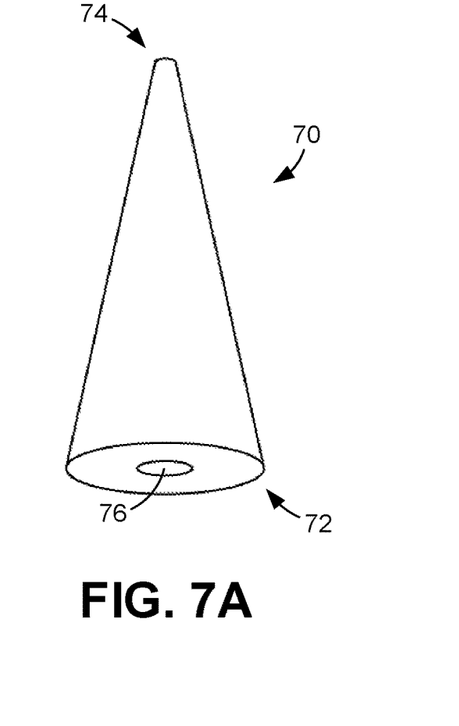
FIG. 7A is a side perspective view of a first alternative dilation tip.
Figure 7B:
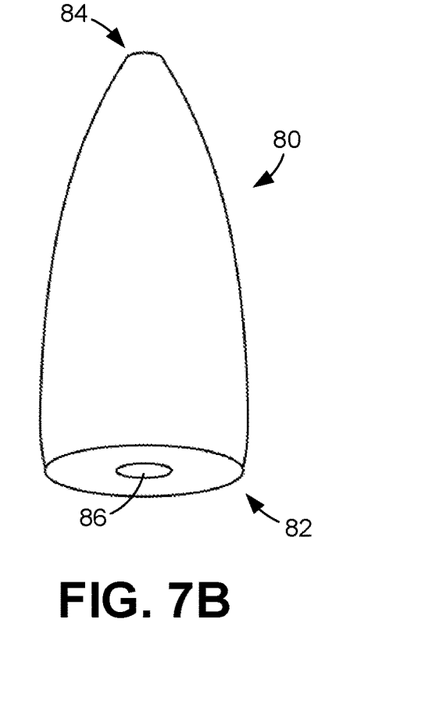
FIG. 7B is a side perspective view of a second alternative dilation tip.

FIGS. 7A and 7B illustrate two examples of alternative configurations for the dilation tip. In FIG. 7A, a dilation tip 70 has a conical configuration in which the diameter of the tip tapers at a constant rate from its proximal end 72 to its distal end 74. Also shown in the figure is an internal passage 76 of the tip. In FIG. 7B, a dilation tip 80 has a rounded conical configuration in which the diameter of the tip tapers at an increasing rate as the tip is traversed from its proximal end 82 to its distal end 84. This tip 80 also includes an internal passage 86.

Figure 8:
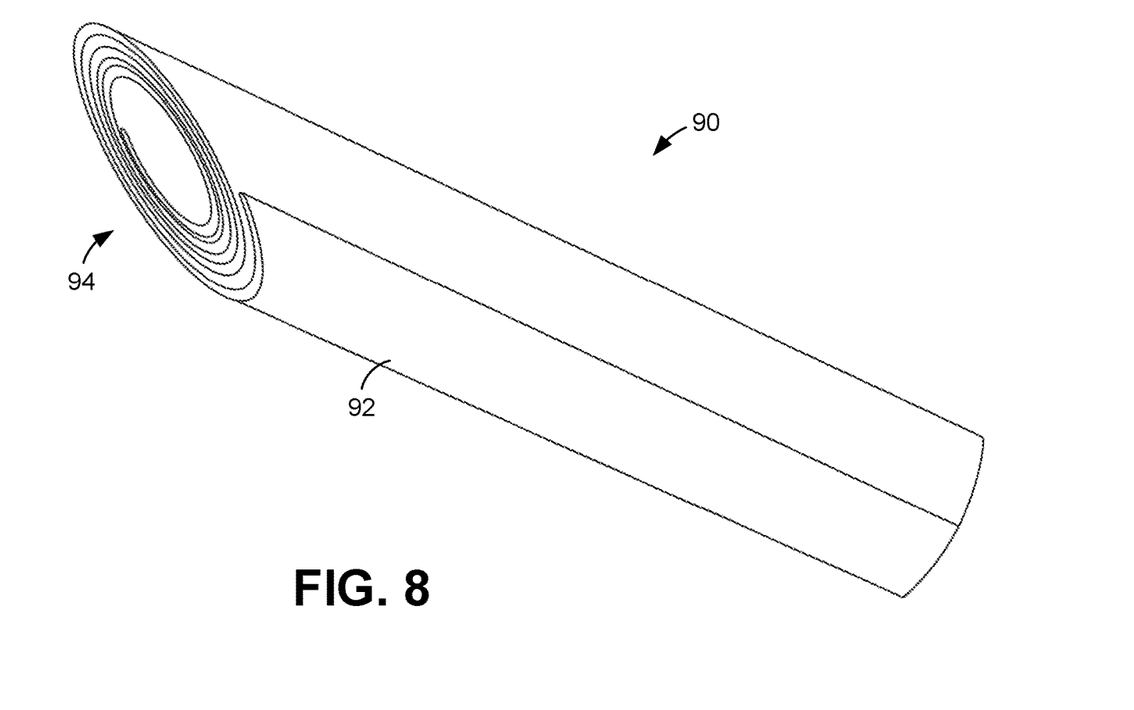
FIG. 8 is a side perspective view of a second alternative expandable access sheath.

Referring next to FIG. 8, illustrated is a second alternative expandable access sheath 90. The access sheath 90 comprises a sheet 92 of material that has been tightly rolled up so as to have a generally cylindrical tube, as described above. In this embodiment, however, the distal end of the rolled sheet 92 has been cut at an oblique angle so as to form a beveled distal end 94. In cases in which the access assembly comprises such an access sheath 90, the beveled distal end 94 facilitates tissue penetration and a separate dilator tip may not be necessary.

Figure 9A:
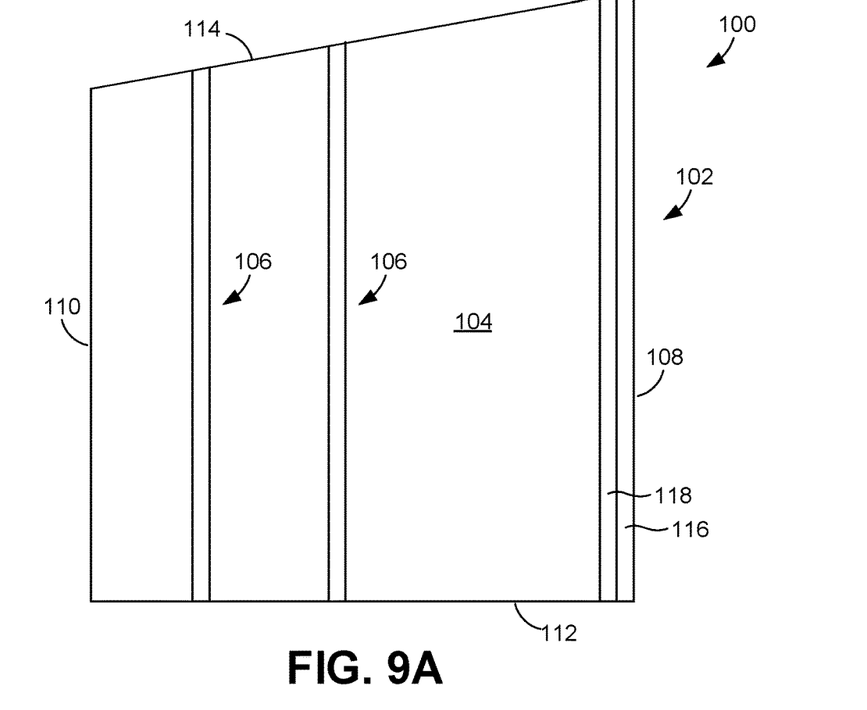
FIG. 9A is a plan view of a third alternative expandable access sheath.
Figure 9B:
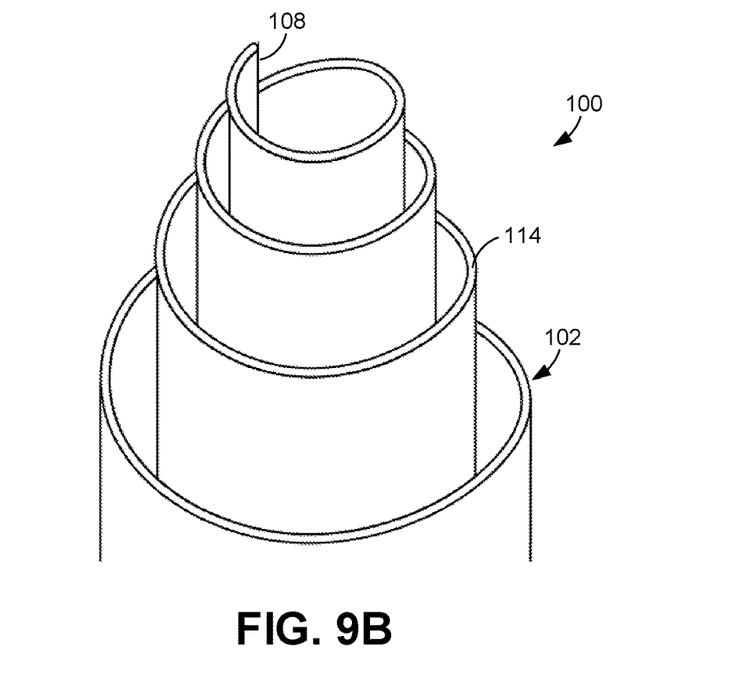
FIG. 9B is a side perspective view of the access sheath of FIG. 9A, the access sheath being shown partially rolled up.

FIGS. 9A and 9B illustrate a third alternative expandable access sheath 100. Beginning with FIG. 9A, the sheath 100 comprises a generally planar sheet 102 of material that forms an inner side 104 on which are provided locking tabs 106. In addition, the sheet 102 includes leading edge 108, a trailing edge 110, a proximal edge 112, and a distal edge 114. The leading edge 108 includes an outermost sharp beveled portion 116 and a bulbous portion 118, which are configured to interface with and lock to one of the locking tabs 106. In this embodiment, however, the distal edge 114 is not parallel to the proximal edge 112. Instead, the distal edge 114 is obliquely configured and forms an angle relative to the proximal edge 112 such that the leading edge 108 is longer than the trailing edge 110. In such a case, the distal end of the sheath forms a conical shape when rolled up, as depicted in FIG. 9B. As with the embodiment of FIG. 8, this facilitates penetration of tissue and a separate dilator tip may not be necessary.

Figure 10:
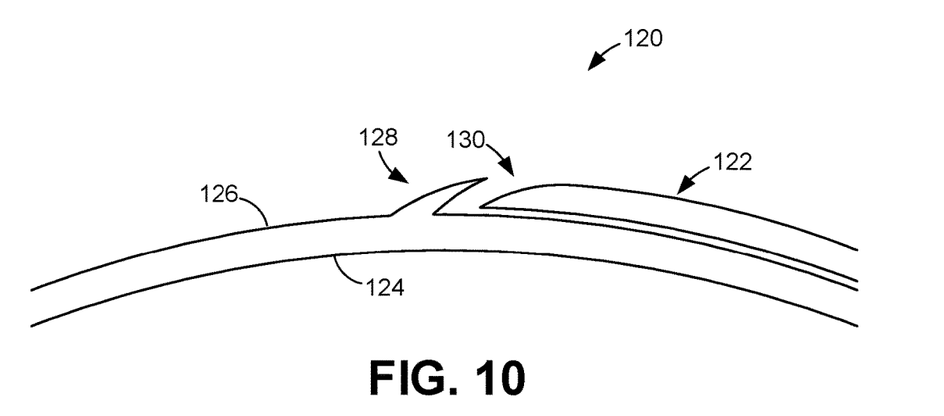
FIG. 10 is a partial side view of a fourth alternative expandable access sheath.

Referring next to FIG. 10, a fourth alternative expandable access sheath 120 is shown. The sheath 120 is similar to the sheath 26 illustrated in FIG. 2. Accordingly, the sheath 120 comprises a generally planar sheet 122 of material that includes an inner side 124 and an outer side 126. In this embodiment, however, the locking tabs, such as locking tab 128, are provided on the outer side 126 of the sheet 122 instead of the inner side 124. The access sheath 120 functions in the same way as the sheath 26, although the leading edge 130 of the sheet 122 interfaces with and locks to the locking tab 128 outside of the working channel that the sheath forms when expanded. While the locking tabs of this embodiment are on the outside of the access sheath 120 and, therefore, are placed in a position in which they interface with patient tissues, the outer casing, when provided, compresses and smooths the locking tabs to ensure that they do not cause trauma to those tissues.

Figure 11:
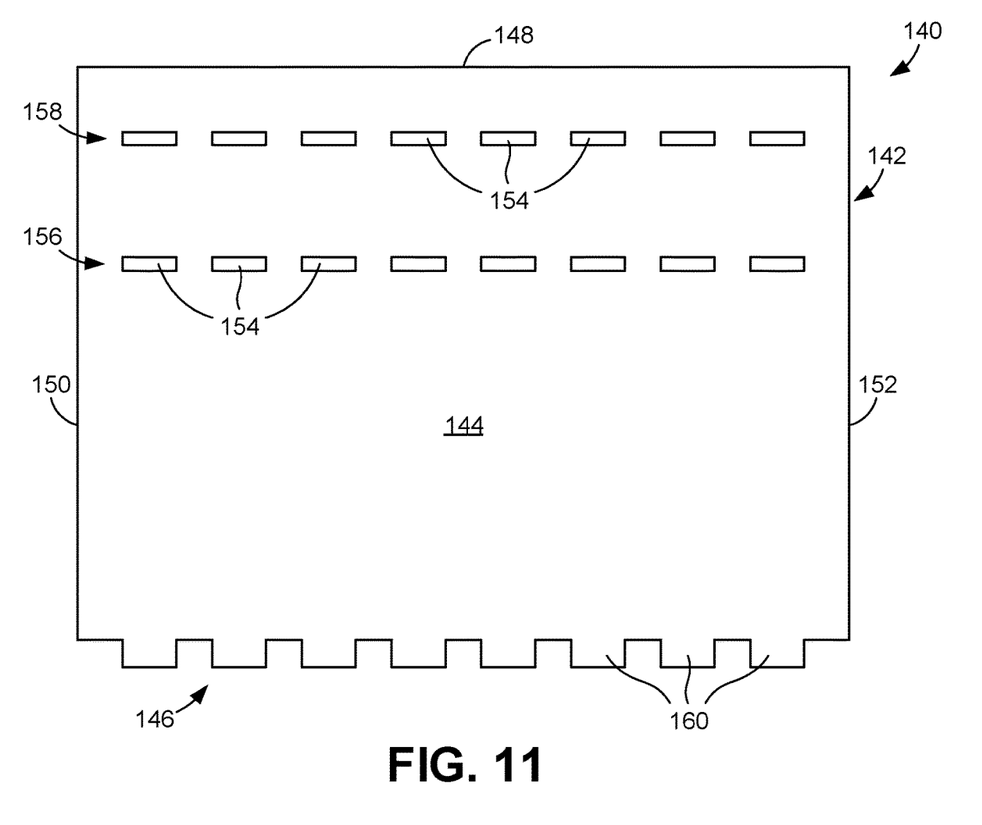
FIG. 11 is a plan view of a fifth alternative expandable access sheath.

FIG. 11 illustrates a fifth alternative expandable access sheath 140. As above, the sheath 140 comprises a generally planar sheet 142 of material that forms an inner side 144 and an outer side (not visible in FIG. 11). In addition, the sheet 102 includes leading edge 146, a trailing edge 148, a proximal edge 150, and a distal edge 152. In this embodiment, however, there are no locking tabs that extend out from the inner or outer side of the sheet 142. Instead, the sheet 102 is provided with multiple openings 154 extending through the sheet that are arranged in linear rows 156 and 158 and that extend along the longitudinal direction of the sheath 140 (i.e., the direction extending from the proximal end to the distal end of the sheath when it is rolled up for insertion). These openings 154 are configured to receive locking tabs 160 that are formed along the leading edge 146 of the sheet 142.

Operation of the sheath 140 is similar to that of the sheaths with locking tabs that extend out from the inner or outer side of its sheet. Specifically, as the rolled-up access sheath 140 is expanded through inflation of a balloon that the sheath surrounds, the locking tabs 160 align with and pass into the openings 154 of one of the linear rows 156, 158, each tab being received within one opening. When this occurs, the sheath 140 is locked in that particular orientation so as to provide and maintain an inner working channel.

Figure 12A:
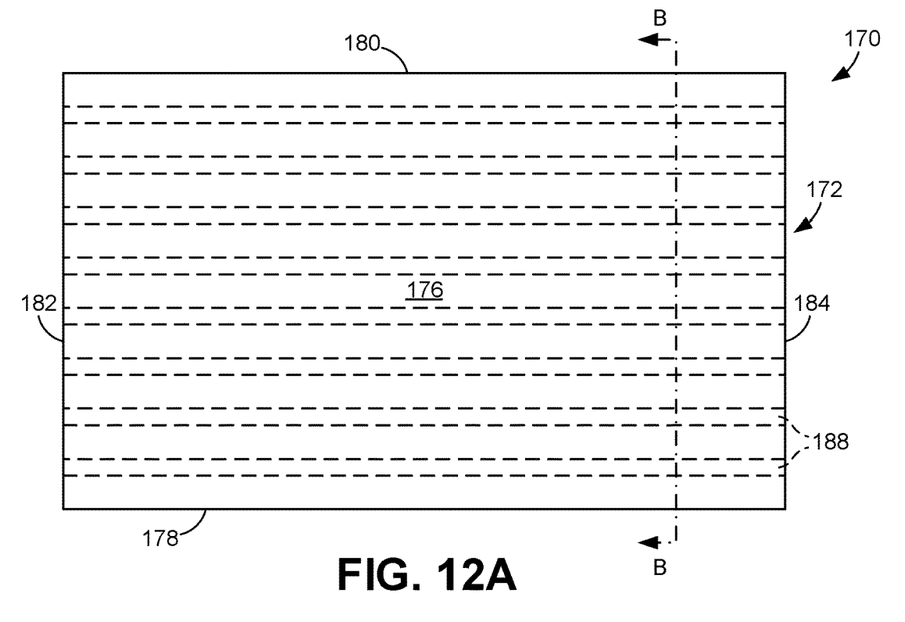
FIG. 12A is a plan view of a sixth alternative expandable access sheath.
Figure 12B:
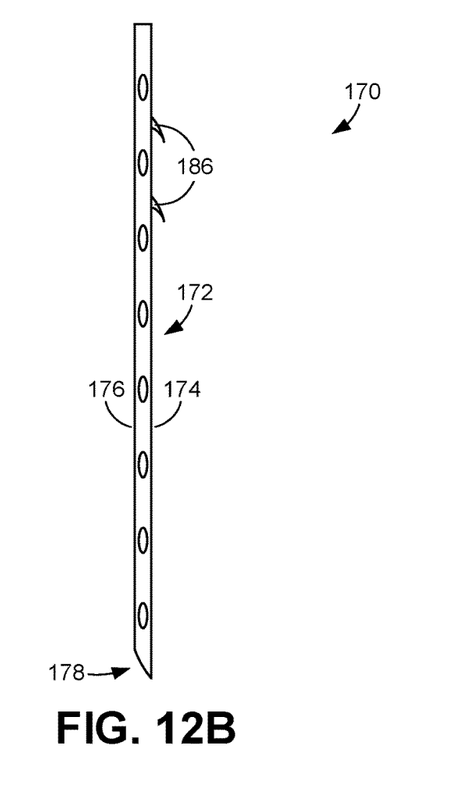
FIG. 12B is an end view of the access sheath of FIG. 12A.

With reference next to FIGS. 12A and 12B, illustrated is a sixth alternative expandable access sheath 170. Once again, the sheath 170 comprises a generally planar sheet 172 of material that forms an inner side 174, an outer side 176, a leading edge 178, a trailing edge 180, a proximal edge 182, and a distal edge 184. As shown in FIG. 12B, extending from the inner side 174 are locking tabs 186 that are configured to receive the leading edge 178, which can be specifically configured for that purpose. In this embodiment, however, the sheet 172 is a flexible fabric sheet that is reinforced along its longitudinal direction (i.e., the direction extending from the proximal end to the distal end of the sheath when it is rolled up for insertion) by multiple spaced inner reinforcing ribs 188 that provide columnar strength to the rolled-up sheath. The ribs 188 can be made of any biocompatible rigid or semirigid (i.e., stiff but still capable of flexing) material such as a metal or polymeric material. Regardless of the material that is used, the ribs 188 provide structural integrity to the sheath 170 to prevent it from buckling during insertion. In the illustrated embodiment, the ribs 188 are elliptical in cross-section, although it is noted that other shapes are possible.

Figure 13:
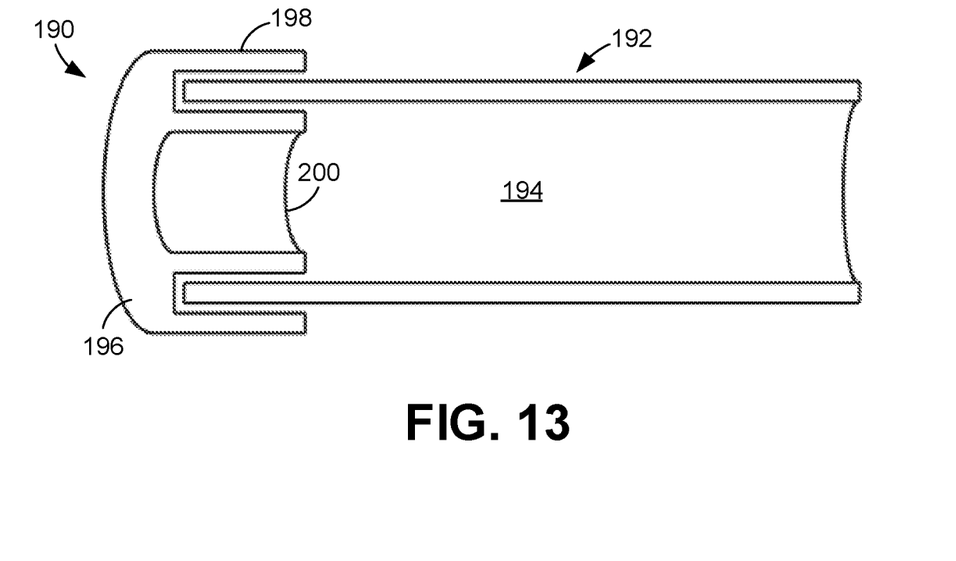
FIG. 13 is a cross-sectional perspective view illustrating an end cap provided on a proximal end of a rolled up access sheath.

Irrespective of the particular configuration of the expandable access sheath, an end cap can be attached to the proximal end of the expanded sheath to maintain its configuration and the size of the working channel it has formed. FIG. 13 shows an example of such an end cap 190. In this figure, the end cap 190 is shown mounted to the proximal end of an expanded access sheath 192 that forms an inner working channel 194. The end cap 190 includes a circular base 196. Extending from the periphery of the base 196 is a continuous arcuate outer wall 198 that is configured to surround the proximal end of the expanded sheath 192. Extending from a central portion of the base 196 is a continuous arcuate inner wall 200 that is configured to be received within the proximal end of the working channel 194. Accordingly, the proximal end of the expanded sheath 192 is held between the outer and inner walls 198, 200 of the end cap 190 to prevent the sheath from expanding or contracting, thereby maintaining the inner dimension (e.g., inner diameter) of the working channel 194. Notably, multiple end caps 190 can be supplied along with each sheath 192, one being sized for each expanded size of the sheath. Accordingly, regardless of the size of the working channel 194 that is formed using the locking means of the access sheath, an end cap 190 will be available to maintain that size.

Figure 14:
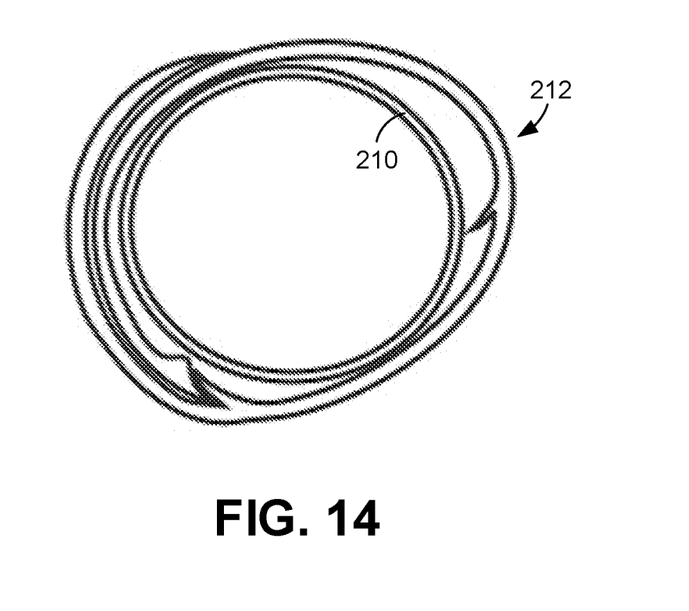
FIG. 14 is an end view illustrating an auxiliary access sheath being provided within an expandable access sheath similar to that shown in FIG. 2.

FIG. 14 illustrates the use of an auxiliary access sheath 210. As is apparent from FIG. 14, this sheath 210 has been inserted into an expandable access sheath 212 of the type described above. The auxiliary access sheath 210 is configured as a simple rigid or semirigid tube that is incapable of expansion. Use of such an auxiliary access sheath 210 inside an expandable access sheath 212 may be desirable for several reasons. First, if the auxiliary access sheath 210 has greater structural integrity than that of the expanded access sheath 212, use of the auxiliary access sheath will help maintain patency of the working channel and resist collapse from the forces imposed by the patient's tissues. Second, as the auxiliary access sheath 210 is a simple tube, there are no features within the sheath, such as locking means, that could interfere with performance of the surgical procedure.

As noted above, the disclosed access systems are not limited to use in percutaneous nephrolithotomy. Other example procedures include mitral valve placement, the formation of expandable retractors for cranial or spinal surgeries, abscess drainage, tube placement, and intra-corporeal entry for laparoscopic, robotic, hysteroscopic, obstetric, fetal, vascular, and other percutaneous surgeries. Furthermore, while the inflatable balloon and the access sheath have been described as discrete components, it is noted that, in other embodiments, these two components can be integrated together into a single component. For example, the balloon can be attached to the inner surface of the access sheath. In such a case, a further dilator can be used to press the deflated balloon against the inner surface of the access sheath to achieve an open working channel.

The invention claimed is:

1. An access assembly comprising:
   an inflatable balloon having a first internal passage configured to receive a guidewire;
   a dilation tip mounted to the inflatable balloon, the dilation tip having a second internal passage aligned with the first passage that is also configured to receive a guidewire; and
   an expandable access sheath wrapped around the inflatable balloon, the access sheath comprising a flexible planar sheet of material that is rolled up to form a cylindrical tube, the flexible planar sheet of material comprising an inner surface, an outer surface, a leading edge, and a trailing edge, each of which being unitarily formed with and by the flexible planar sheet of material, the flexible planar sheet of material further comprising at least one locking tab that extends from the inner side or the outer side of the flexible planar sheet of material that is configured to directly mate with the leading edge of the flexible planar sheet of material to lock the access sheath in a predetermined configuration and form an inner working channel having a predetermined cross-sectional dimension through which a surgical procedure can be performed, wherein the access sheath is configured to expand when the balloon is inflated to place the leading edge of the flexible planar sheet of material in a position at which it can mate with the at least one locking tab.

2. The assembly of claim 1, wherein the locking tab extends from the inner side of the sheet.

3. The assembly of claim 1, wherein the locking tab extends from the outer side of the sheet.

4. The assembly of claim 1, wherein the leading edge comprises a beveled portion that is configured to mate with the locking tab.

5. The assembly of claim 4, wherein the leading edge further comprises a bulbous portion inward of the beveled portion, the bulbous portion being configured to form a smooth transition between the locking tab and the surface of the sheet.

6. The assembly of claim 1, wherein the sheet comprises multiple locking tabs positioned at discrete positions along the inner or outer surface of the sheet so as to be configured to lock the access sheath in multiple predetermined configurations, each forming an inner working channel having a predetermined cross-sectional dimension.

7. The assembly of claim 1, wherein the locking tab comprises multiple spaced locking tab segments that are linearly aligned with each other so as to form the locking tab.

8. The assembly of claim 1, further comprising an elastic outer casing wrapped around the expandable access sheath that squeezes the access sheath to assist with mating of the leading edge and the at least one locking tab upon deflation of the balloon.

9. An expandable access sheath comprising:
   a flexible planar sheet of material that is configured to be rolled up around an inflatable balloon, the flexible planar sheet of material comprising an inner surface, an outer surface, a leading edge, a trailing edge, a proximal edge, and a distal edge, each of which being unitarily formed with and by the flexible planar sheet of material, the flexible planar sheet of material further comprising at least one locking tab that extends from either the inner surface or the outer surface of the flexible planar sheet of material, wherein the leading edge of the flexible planar sheet of material is configured to directly mate with the locking tab to lock the access sheath in a predetermined configuration in which the access sheath forms an inner working channel having a predetermined cross-sectional dimension after the access sheath has been expanded by the inflatable balloon.

10. The access sheath of claim 9, wherein the locking tab extends from the inner side of the sheet.

11. The access sheath of claim 9, wherein the locking tab extends from the outer side of the sheet.

12. The access sheath of claim 9, wherein the leading edge comprises a beveled portion that is configured to mate with the locking tab.

13. The access sheath of claim 12, wherein the leading edge further comprises a bulbous portion inward of the beveled portion, the bulbous portion being configured to form a smooth transition between the locking tab and the surface of the sheet.

14. The access sheath of claim 9, wherein the sheet comprises multiple locking tabs positioned at discrete positions along the inner or outer surface of the sheet so as to be configured to lock the access sheath in multiple predetermined configurations, each forming an inner working channel having a predetermined cross-sectional dimension.

15. The access sheath of claim 9, wherein the locking tab comprises multiple spaced locking tab segments that are linearly aligned with each other so as to form the locking tab.

16. The access sheath of claim 9, wherein the leading edge is parallel with the trailing edge but the distal edge is angled relative to the proximal edge such that the access sheath forms a conical distal end when the access sheet is rolled up.

17. A method for performing a surgical procedure, the method comprising:
forming a passage through soft tissues of a subject to a site of interest at which the surgical procedure is to be performed;
passing a guidewire through the passage;
passing an access assembly over the guidewire and into the passage, the access assembly comprising an inflatable balloon and an expandable access sheath that surrounds the balloon, the access sheath comprising a flexible sheet of material that is rolled up around the balloon, the flexible sheet of material comprising a leading edge that is unitarily formed with and by the flexible sheet of material and a locking tab that extends from a side of the flexible sheet of material;
inflating the balloon to expand the access sheath to an extent at which the leading edge of the flexible sheet of material can mate with the locking tab;
deflating the balloon to enable the leading edge of the flexible sheet of material to directly mate with the locking tab, thereby locking the access sheath in a predetermined configuration at which the access sheath forms an inner working channel having a predetermined cross-sectional dimension;
removing the balloon from the working channel; and
performing the surgical procedure at the site of interest with surgical instruments that are passed through the working channel.

18. The method of claim 17, wherein the access assembly further comprises an elastic outer casing wrapped around the expandable access sheath that squeezes the access sheath to assist with mating of the leading edge and the at least one locking tab upon deflation of the balloon.

\* \* \* \* \*